(12) United States Patent
Bruder et al.

(10) Patent No.: US 7,058,156 B2
(45) Date of Patent: Jun. 6, 2006

(54) IMAGING METHOD FOR A MULTI-SLICE SPIRAL CT SCAN WITH 3D RECONSTRUCTION, AND A COMPUTED TOMOGRAPHY UNIT FOR CARRYING OUT THIS METHOD

(75) Inventors: Herbert Bruder, Hoechstadt (DE); Thomas Flohr, Uehlfeld (DE); Stefan Schaller, Fuerth (DE); Karl Stierstorfer, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 201 days.

(21) Appl. No.: 10/686,596

(22) Filed: Oct. 17, 2003

(65) Prior Publication Data
US 2004/0131142 A1 Jul. 8, 2004

(30) Foreign Application Priority Data
Oct. 18, 2002 (DE) .............................. 102 48 770

(51) Int. Cl.
*A61B 6/03* (2006.01)
(52) U.S. Cl. .......................................... 378/15; 378/8
(58) Field of Classification Search .................... 378/8, 378/15, 901
See application file for complete search history.

(56) References Cited

U.S. PATENT DOCUMENTS

| 5,926,521 | A | * | 7/1999 | Tam | 378/4 |
| 6,018,561 | A | * | 1/2000 | Tam | 378/4 |
| 6,084,937 | A | * | 7/2000 | Tam et al. | 378/4 |
| 6,130,930 | A | * | 10/2000 | Tam | 378/4 |
| 6,275,561 | B1 | * | 8/2001 | Danielsson | 378/15 |
| 6,490,335 | B1 | * | 12/2002 | Wang et al. | 378/15 |
| 2002/0141628 | A1 | | 10/2002 | Bruder et al. | |

FOREIGN PATENT DOCUMENTS

DE 10126638 5/2001

OTHER PUBLICATIONS

H. Turbell, P.E. Danielsson, An improved PI-method for reconstruction from helical cone-beam projections, Proc. Int. Conf. On Fully 3D image Reconstruction, Egmond and Zee, The Netherlands, Jun. 23-26, 1999.
German Office Action dated Oct. 1, 2003.

* cited by examiner

*Primary Examiner*—David V Bruce
(74) *Attorney, Agent, or Firm*—Harness, Dickey & Pierce, P.L.C.

(57) ABSTRACT

An imaging method is for a multi-slice spiral CT scan with 3D back projection. Use is made, for the reconstruction of the absorption value of at least one voxel, of the measured and filtered data that are produced by rays which penetrate the at least one voxel. A CT unit is further used to carry out the method. In the method, the filtering of the data, required for the reconstruction, in the image of the virtual detector is performed in the direction of the projection of spiral segments imaged thereon which are produced by the spiral scanning over a prescribed angular range. The CT unit includes a device for carrying out directional filtering of this type.

49 Claims, 5 Drawing Sheets

IMAGING METHOD FOR A MULTI-SLICE SPIRAL CT SCAN WITH 3D RECONSTRUCTION, AND A COMPUTED TOMOGRAPHY UNIT FOR CARRYING OUT THIS METHOD

The present application hereby claims priority under 35 U.S.C. §119 on German patent application number DE 102 48 770.7 filed Oct. 18, 2002, the entire contents of which are hereby incorporated herein by reference.

FIELD OF THE INVENTION

The invention generally relates to an imaging method for a multi-slice spiral CT scan with 3D back projection. An object to be examined may be scanned spirally with reference to its absorption behavior by way of a rotating ray bundle moving in the direction of the axis of rotation. The measured absorption data may be collected by the detector of planar design. The measured absorption data are projected onto a virtual detector, preferably at the fulcrum of the rotation, and filtered, and for the reconstruction of the absorption value of at least one voxel use is made of those measured and filtered data that have been produced by rays which penetrate this at least one voxel. The invention also generally relates to a CT unit for carrying out this method and having appropriate imaging device.

The invention also generally-relates to a CT unit for carrying out this method and having corresponding imaging device.

BACKGROUND OF THE INVENTION

It is known to make use in computed tomography of multi-slice detectors and ray bundles with cone geometry for the purpose of scanning objects to be examined, in particular patients, and to carry out a 3D image reconstruction. In this process, integral absorption data of rays that penetrate the object to be examined are acquired and collected by multi-row detectors of planar design, the detectors being moved spirally, together with a radiation source, about an object to be examined. Subsequently, the measured data are subjected to suitable filtering, and selected filtered data are back projected in order to produce tomographic images of the object to be examined. In this case, 3D image reconstruction means that for the purpose of back projection individual three-dimensional volume elements (=voxel) are considered in each case, and use is made in each case of the data that have been produced by rays and which have penetrated this voxel.

This mode of procedure is attended by the problem that because the collected data, which are firstly projected, for the purpose of simplifying calculation, onto a virtual detector—which lies on a plane that intersects the axis of rotation of the real detector and radiation source—are present in two dimensions and the filtering is intended to take place only in one dimension because of the resultant outlay on computation, there is no preferred direction to be seen in which the filtering should take place. If an unfavorable filtering direction is selected, it is therefore accompanied by losses in image quality.

SUMMARY OF THE INVENTION

It is therefore an object of an embodiment of the invention to find a 3D reconstruction method in which the direction of filtering is selected optimally in order to achieve high image quality.

A consideration of the image of a virtual detector with projections, imaged thereon, of segment planes such as are defined below and are described, for example, in DE 101 26 638 A1, the entire content of which is hereby incorporated herein by reference, shows that the direction of the projections varies over the virtual detector. According to an embodiment of the invention, the filtering of the data in the direction of these projections is carried out on the virtual detector. If, furthermore, consideration is given to the path of the projection of a voxel on the virtual detector during rotation, this projected voxel runs through zones of different alignment of the segment plane projections. It is particularly favorable in this case to undertake the filtering of the data respectively along the alignment of the segment plane projections such that different filtering directions are produced as a function of the angle of projection.

Considering a 3D reconstruction such as described in DE 101 26 638 A1, $N_{tilt}$ multiply inclined segment planes are fitted into the spiral pitch in a spiral segment of length $L_s \leq \Pi + 2*\beta_{max}$ (=180° plus twice the fan angle $\beta_{max}$ of the detector), or $\leq 180°$ after preceding parallel sorting. The maximum inclination of the segment planes $R_k$ ($121 \leq k \leq N_{tilt}$) is determined in this case from the condition that rays must be present for the plane at the two ends of the spiral segment within the measuring field. For example, it then holds for Ls=240° (where $\beta_{max}=30°$), and for Ls=180° after parallel sorting that $N_{tilt}=\lceil 2 \cdot M/p \rceil$, where M is the number of detector rows and p the pitch of the spiral.

According to an embodiment of the invention, the filtering direction of the data is defined by the intersection lines, determined in the spiral segment at the spacing $\Delta\alpha=L_s/M$, of the segment planes in the virtual detector at the fulcrum.

The virtual detector is completely covered if the spiral segment is widened on the left and on the right for k=1 and k=$N_{tilt}$, respectively. A separately filtered detector image is attained in this way for each segment plane $R_k$ ($1 \leq k \leq N_{tilt}$). This filter operation is performed in each of the detector images measured by projection, the detector images Dk responsible for the back projection for different subsegments of the reconstruction interval.

A spiral segment $I_I$ of the length $L_I=[-\alpha_{max}, \alpha_{max}]$ where $\alpha_{max}=M\cdot\pi/p$, is subdivided from the 3D back projection into $N_{tilt}$ overlapping subsegments $I_I^k$ ($1 \leq k \leq N_{tilt}$) of length $L_s$, their centroids differing from one another by at most $L_s$ and being subdivided equidistantly. The segment $I_I$ is fitted centrally into the reconstruction segment $I_I$. This results in the following for the subsegments $I_R^k$ ($1 \leq k \leq N_{tilt}$):

$$I_R^k = I_I^k; \quad 1 < k < N_{tilt}$$

$$I_R^1 = I_I^1 \cup \{-\alpha^v\text{max}, -\alpha\,\text{max}\}$$

$$I_R^{Ntilt} = I_I^{Ntilt} \cup \{\alpha\,\text{max}, \alpha^v\,\text{max}\}$$

such that the projection datum, belonging to an image voxel, in the detector image $D_k$ is determined by projection in the reconstruction segment $I_R^k$, where $1 \leq k \leq N_{tilt}$.

It is advantageous to track the image of a voxel in the virtual detector in a reconstruction segment $I_R$ in order to illustrate this idea of an embodiment of the invention. Considering firstly the spiral segment $I_R^1$ and the projection angle $\alpha=-\alpha_{max}$, the detector images $D_1$ are responsible for the back projection in this spiral segment in terms of projection. All voxels that are imaged in the virtual detector at the projection angle $\alpha=-\alpha_{max}$ in the selected filtering direction according to an embodiment of the invention form a curved surface $H_1$.

The filtering direction at $\alpha=\oplus\alpha_{max}$ is given by the image of the segment plane $R_1$ centered at the projection angle $\alpha=-\alpha_{max}+L_S/2$ and fitted into the spiral pitch. The image of the curved surface $H_1$ is not a straight line in the virtual detector for $\alpha>-\alpha_{max}+L_s/2$. It has been shown in the publication by H. Turbell, P. E. Danielsson, entitled An improved PI-method for reconstruction from helical cone-beam projections, Proc. Int. Conf. On Fully 3D image Reconstruction, Egmond and Zee, The Netherlands, Jun. 23–26, 1999, the entire contents of which are hereby incorporated herein by reference, that the segment plane $R_1$ constitutes a good approximation of the curved surface $H_1$. Consequently, in all other projections in the spiral segment $I_R^1$ the image $H_1$ in the virtual detector is grouped around the corresponding intersection line of $R_1$. Thus, the filtering directions of $D_1$ that are given by the image of $R_1$ in the virtual detector are suitable for all the remaining projection angles in the subsegment $I_R^1$. The above argument is valid in like fashion for all the remaining subsegments $I_R^k$ ($1 \leq k \leq N_{tilt}$).

In accordance with this basic idea, the inventors propose to improve the imaging method, known per se, for a multi-slice spiral CT scan. It is known that:

an object to be examined is scanned spirally with reference to its absorption behavior i.e. rotating ray bundle moving in the direction of the axis of rotation, and the measured absorption data are collected by a detector of planar design, the measured absorption data are projected onto a virtual detector, preferably at the fulcrum of the rotation, and filtered, and in order to reconstruct the absorption value of at least one voxel, use is made of the measured and filtered data that are produced by rays that penetrate this at least one voxel.

The improvement in the method resides in the particular selection of the filtering direction, in that the filtering of the data, used for the reconstruction, in the image of the virtual detector is performed in the direction of the projection of spiral segments that are imaged thereon and which are produced by the spiral scanning over a prescribed angular range.

The result of this is that different and in each optimum filtering directions occur for the data of different reconstruction segments of a voxel, in which case there is the additional advantage that the pitch of the spiral of the selection of the bed feed is arbitrary. It is therefore possible to consider overlapping scanning in the z-direction.

In a preferred design of the method, the filtering takes place along the intersection line of doubly inclined planes in the virtual detector.

In accordance with a further preferred design of the method, the prescribed angular range is swung ~240° for a spiral segment of length $L_s$, the angle 240° corresponding to the sum of 180°+2×fan angle $\beta_{max}$ that is necessary for the reconstruction of an image voxel.

Alternatively, it is also proposed to carry out parallel sorting of the rays in order to form the virtual detector before filtering, the prescribed angular range for a spiral segment of length Ls being 180°.

Furthermore, the segment planes formed at least approximately by the spiral segments can have a maximum inclination that is limited by the condition that rays for the plane must be present at the two ends of the spiral segment within the measuring field.

In addition, for the purpose of 3D back projection it is advantageous to subdivide a spiral segment $I_I$ of length $L_I=[-\alpha_{max},+\alpha_{max}]$ with $\alpha_{max}=M\cdot\pi/p$ into $N_{tilt}$ overlapping subsegments $I_I^k$ ($1 \leq k \leq N_{tilt}$) of length $L_S$, whose centroids differ from one another by at most $L_S$, p corresponding to the set pitch, such that the following holds for the subsegments $I_R^k$ ($1 \leq k \leq N_{tilt}$) produced:

$I_R^k = I_1^k; 1 < k < N_{tilt}$ $I_R^1 = I_I^1 \cup \{-\alpha^v \max, -\alpha \max\}$ $I_R^{Ntilt} = I_I^{Ntilt} \cup \{\alpha \max, \alpha^v \max\}$ and the projection datum, belonging to an image voxel, in the detector image $D_k$ is determined by projection in the reconstruction segment $I_R^k$ ($1 \leq k \leq N_{tilt}$), $\alpha^v_{max}$ representing the maximum angle reached by the ray through the voxel V. The projection datum corresponds to the projection value that is found in the detector and which corresponds to the image of the image voxel in the detector, the image of the point of intersection of the ray from the focus through the image voxel being in the detector.

If, in addition, consideration is given to the path, of somewhat different length, of the rays through the object to be examined as a function of the cone angle of the ray bundle used, it emerges as advantageous to weigh the measured absorption data as a function of the cone angle of the ray produced in the direction of the axis of rotation of the detector and radiation source, preferably with the a cosine of its cone angle.

The detector of planar design used for the spiral scanning of the object to be examined can be provided with a multiplicity of detector elements that are arranged matricially in rows and columns. However, there is also the possibility in principle of differently fashioned distributions of the detector elements over the detector, for example, in a helical arrangement or in an arrangement with detector rows of different width that can also, if appropriate, have detectors of different extent in the direction of rotation and directional pitch.

In addition to the method according to an embodiment of the invention, the inventors also propose a CT unit for scanning an object to be examined. Such a unit may be equipped with a ray bundle emanating from at least one focus, and with a detector array of planar design and having a multiplicity of distributed detector elements for detecting the rays of the ray bundle, the at least one focus moving relative to the object to be examined on at least one focus track with the detector array opposite. It may further include at least a device for collecting detector data, with filtering and 3D back projection being provided. The device for filtering may be fashioned in such a way that the method is carried out. The device for filtering can be implemented at least partially by programs or program modules.

The overall result of the use of the method according to an embodiment of the invention and of the inventive CT unit is that an improved image quality is attached by the particular selection of the filtering direction.

BRIEF DESCRIPTION OF THE DRAWINGS

The present invention will become more fully understood from the detailed description of preferred embodiments given hereinbelow and the accompanying drawings, which are given by way of illustration only and thus are not limitative of the present invention, and wherein.

DETAILED DESCRIPTION OF THE PREFERRED EMBODIMENTS

Figure 1:
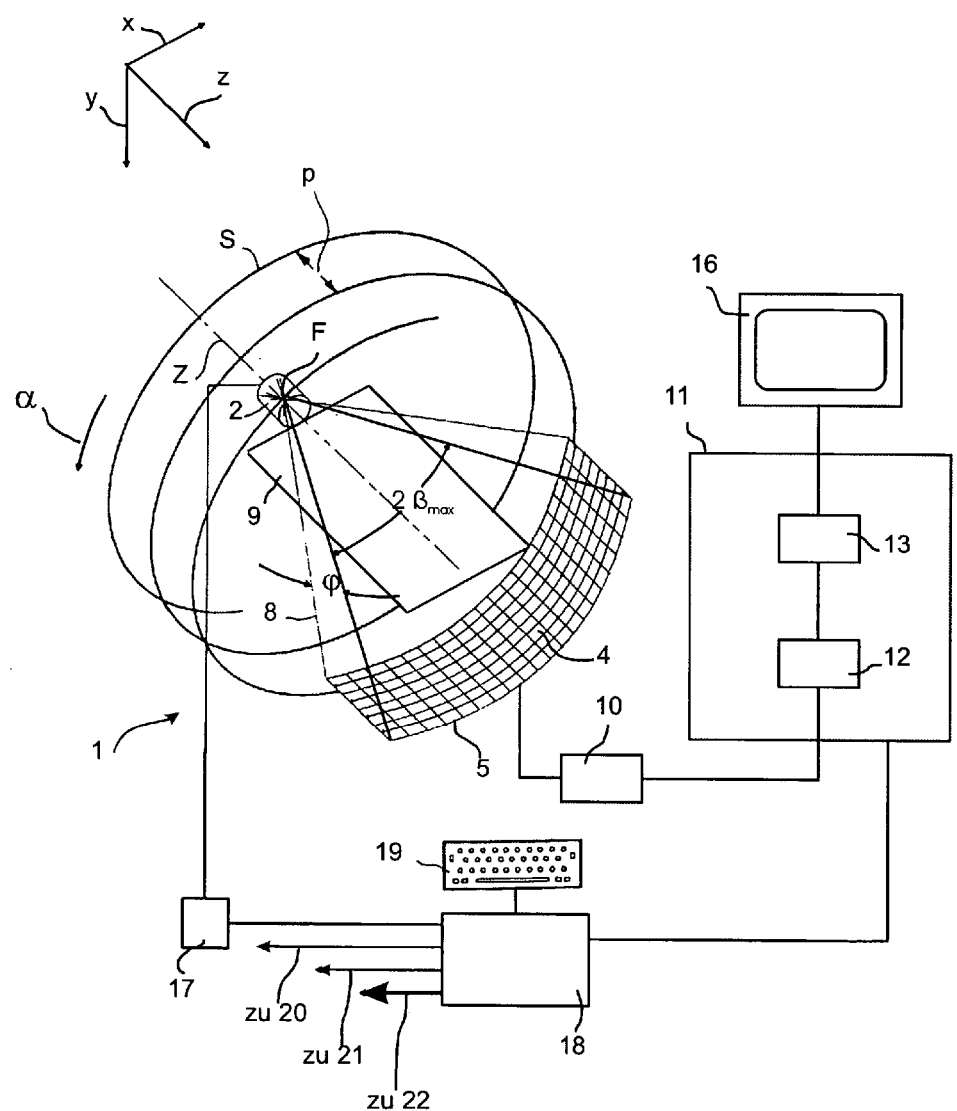
FIG. 1 shows multi-slice CT in a perspective illustration of the scanning unit.
Figure 2:
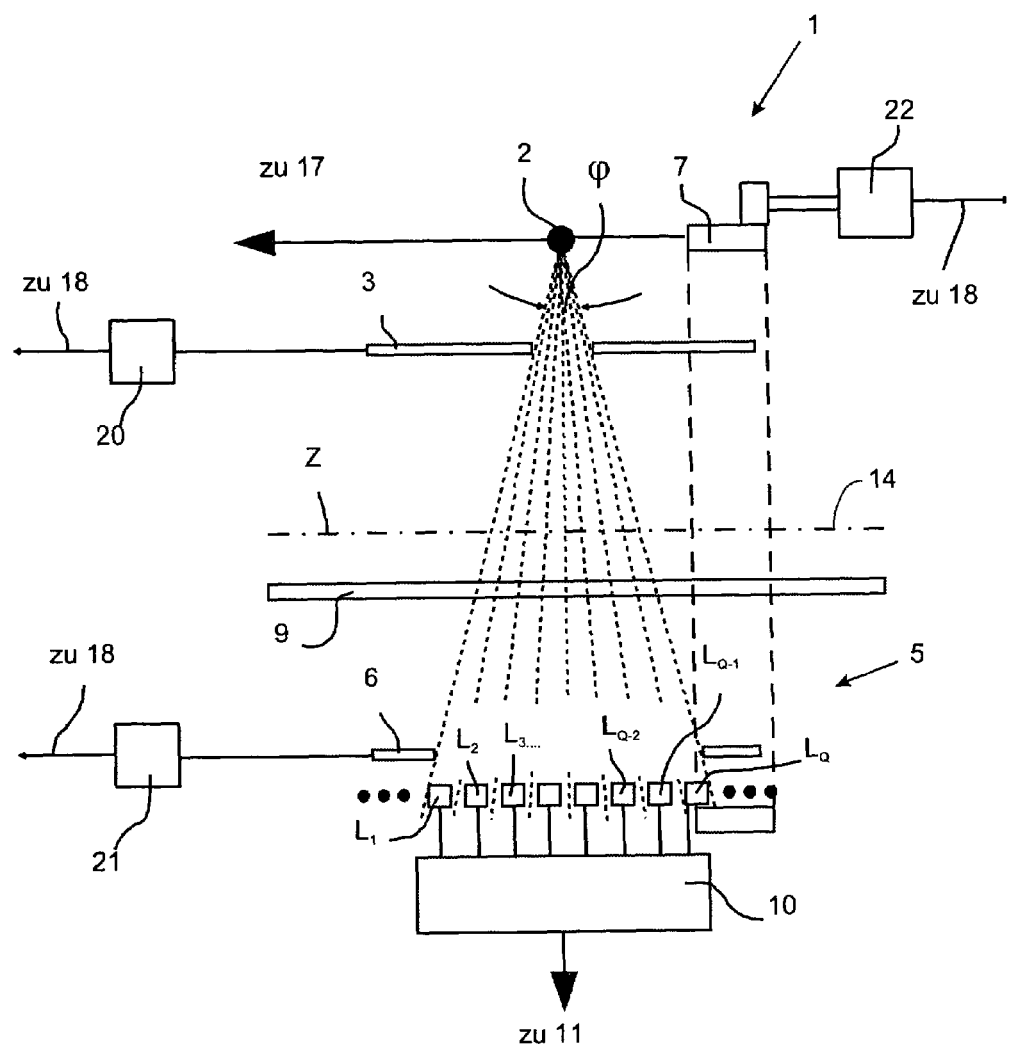
FIG. 2 shows a longitudinal section through the multi-slice CT from FIG. 1.

FIGS. 1 and 2 show a partially perspective illustration of a third generation multi-slice CT unit for carrying out the method according to an embodiment of the invention. The measuring arrangement (=gantry) denoted by 1 has an X-ray source 2 with a beam diaphragm 3 positioned in front of it. This array of planar design having a plurality of rows and columns of detector elements forms a detector system 5 and is illustrated in section in FIG. 2 with a beam diaphragm 6 positioned in front of said detector system and near the detector. For the purpose of greater clarity, FIG. 1 illustrates only eight rows L1 to LQ of detector elements 4. Detector system 5 can, however, also have any other or preferably greater number of rows without departing from the scope of the invention. A different planar arrangement of the detectors is also likewise possible.

The X-ray source 2 with the beam diaphragm 3 on the one hand, and the detector system 5 with the beam diaphragm 6, on the other hand, are fitted on a rotary frame 7 opposite one another in such a way that a pyramidal X-ray bundle whose edge rays are denoted by eight, which emanates from the X-ray source 2 during operation of the CT unit and is stopped down by the adjustable beam diaphragm 3, strikes the detector system 5. In this case, the beam diaphragm 6 is set to correspond to the cross section of the X-ray bundle, set by means of the beam diaphragm 3, such that in the accordance with different operating modes only that region of the detector system 5 is exposed which is struck directly by the X-ray bundle. Only eight rows of detector elements 4 are used in FIGS. 1 and 2, while the further rows, indicated by dots, are covered by the beam diaphragm 6 and therefore not active.

The X-ray bundle has a cone angle $\phi$, which is the aperture angle of the X-ray bundle in a plane containing the system axis Z and the focus F. The aperture angle of the X-ray bundle is $2\beta_{max}$ in a plane (an aperture angle) situated at right angles to the system axis Z and contained in the focus F.

The rotary frame 7 can be set in rotation about a system axis denoted by Z by means of a drive device 22. The system axis Z runs parallel to the z-axis of the coordinate system which is rectangular in three-dimensions and illustrated in FIG. 1.

The columns of the detector system 5 likewise run to the direction of the z-axis, while the rows run transverse to the system axis Z.

In order to be able to bring an object to be examined, for example a patient, into the beam path of the X-ray bundle, a support device 9 is provided which can be displaced parallel to the system axis Z, that is to say in the direction of the z-axis, specifically in such a way as to obtain synchronization between the rotation movement of the rotary frame 7 and the translation movement of the support device such that the ratio of translation speed to rotation speed is adjustable by selecting a desired value of the feed p (=pitch) of the support device 9 per rotation of the rotary frame.

It is hence possible for a volume of an object to be examined, located on the support device 9, to be examined in accordance with a volume scan, it being possible to carry out volume scan in a form of a spiral scan such that a multiplicity of projections from different projection directions are recorded by way of a measuring unit and per revolution of the measuring unit 1, by simultaneous rotation of the measuring unit 1 and translation of the support device 9. During the spiral scan, the focus F of the X-ray source moves relative to the support device 9 on a spiral track denoted by S above the object to be examined. In order to permit a complete reconstruction of a CT image per row of detector elements, the spiral scanning must extent in the α direction over at least $\pi+2\beta_{max}$, but it can also be arbitrary longer within the technical limits of the CT unit.

However, as a consequence of the circumstance that a plurality of rows of detector elements 4 are present, it is also possible for a volume of the object to be examined to be examined in the course of a so called tomogram scanning, in the case of which no relative movement takes place in the direction of the z-axis between the measuring unit 1 and support device 9 (p=0). In the case of the tomogram scanning, therefore, the magnitude of the volume examined is determined by the number of the active rows of detector elements 4. During a tomogram scan, the focus F is moved on a circular focus track or, when the feed is present, a spiral one that lies in a plane denoted below as center plane.

The tomogram scan can be performed as a partial revolution or in the form of a complete revolution, the partial revolution comprising a partial revolution interval of at least $\pi+2\beta_{max}$ (a half revolution plus fan aperture angle), thus permitting a complete reconstruction of a CT image, while a complete revolution comprises $2\pi$.

The measured data which are read out in parallel during the spiral or tomogram scanning from the detector elements of each active row of the detector system 5 and which correspond to the individual projections P ($\alpha,\beta,q$) in fan ray geometry are subjected in a data conditioning unit 10 to digital-to-analog conversion, serialized and transmitted to an image computer 11.

After preprocessing of the measured data in a preprocessing unit 12 of the image computer 11, the resulting data stream passes to a tomographic image reconstruction unit 13 which uses the measured data to reconstruct tomographic images of the desired sections of the object to be examined in a way known per se using a 3D back projection method, the data used firstly being filtered, however.

The CT images are put together from pixels (pixel=picture element) assembled matricially, by pixels being assigned to the respective image plane, each volume being assigned a CT number in Hounsfield units (HU), and it being possible to represent the individual pixels according to the CT number/grey-value scale in a grey-scale value corresponding to its respective CT number. In this case, each pixel illustrates a voxel (voxel=volume element) of the section of the object to be examined illustrated in the CT image. Since measured data are obtained with reference to a plurality of sections of the object to be examined owing to the fact that the detector system 5 has a plurality of rows and, if appropriate, owing to the spiral scanning, 3D data are available, and these are subjected to a 3D back projection within the scope of an embodiment of the invention.

Available as the end result are 3D image data in the form of a three-dimensional matrix, for example with the axes x, y, z, each element of the matrix corresponding to a voxel $V_{(x,y,z)}$ and containing the grey-scale value corresponding to the associated CT number. Those elements of the three-dimensional matrix that have the same x-, y- or z-value then respectively constitute a planar tomographic image of the section of the object to be examined that corresponds to the decisive x-, y- or z-value.

The images reconstructed by the tomographic image reconstruction unit 13 are displayed on a display unit 16, for example a monitor, connected to the image computer 11.

The X-ray source 2, for example an X-ray tube, is supplied by a generator unit 17 with the required voltages and currents, for example the tube voltage U. In order to be able to set these to the respectively required values, the generator unit 17 is assigned a control unit 18 with keyboard 19 that permits the required settings.

The other operation and control of the CT unit is also carried out by way of the control unit 18 and the keyboard 19, and this is illustrated by the fact that the control unit 18 is connected to the image computer 11.

Inter alia, it is possible to set the number of active rows of detector elements 4 and therefore the position on the beam diaphragms 3 and 6, for which the control unit 18 is connected to adjustment units 20 and 21 assigned to the beam diaphragms 3 and 6. It is also possible to set the rotation time τ which the rotary frame 7 requires for the full rotation, and this is illustrated by the fact that a drive unit 22 assigned to the rotary frame 7 is connected to the control unit 18.

Although it is also possible in principle to implement the inventive method by using fan beam geometry as well, the described CT unit is preferably operated in a mode in which the inventive method is implemented using parallel beam geometry.

Consequently, the data obtained from spiral or tomogram scanning using fan beam geometry, the scanning of the body region of the patient relevant for the respective examination are firstly converted in a way known per se into data in terms of parallel beam geometry by using a method denoted in general as "rebinning". This conversion is based on resorting the data obtained using fan beam geometry in such a way that rays are extracted from different projections recorded using fan beam geometry and combined to form a projection in parallel beam geometry. In parallel beam geometry, data from interval of length π suffice to be able to reconstruct a complete image. In order to be able to obtain these data, data must be available in fan beam geometry from an interval of length $\pi+2\beta_{max}$.

Figure 3:
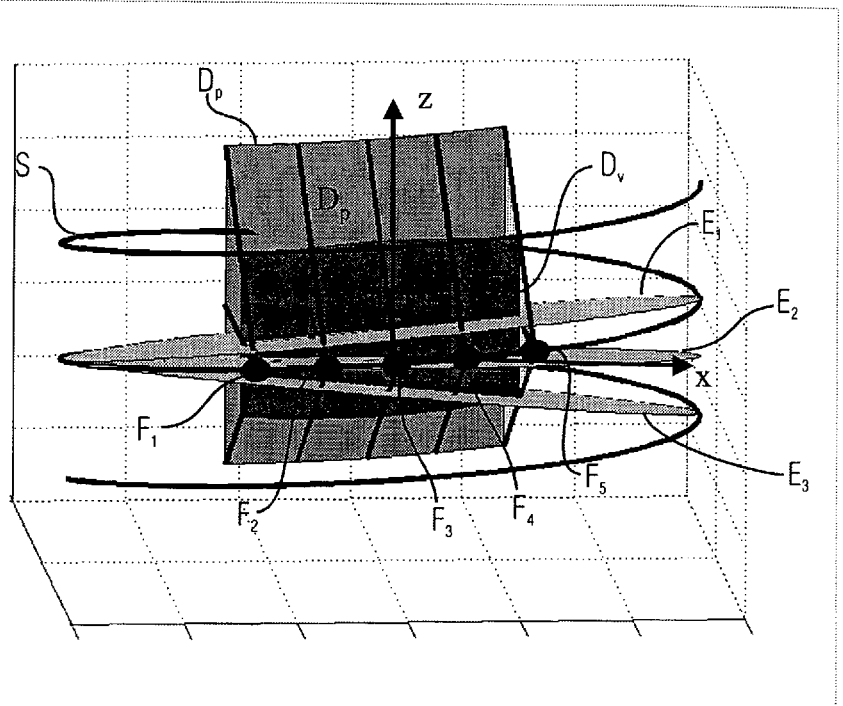
FIG. 3 shows the projection of segment planes in the parallelized representation of a physical detector Dp on a virtual detector Dc with a representation of three intersection volumes and associated spiral segments.
Figure 4A:
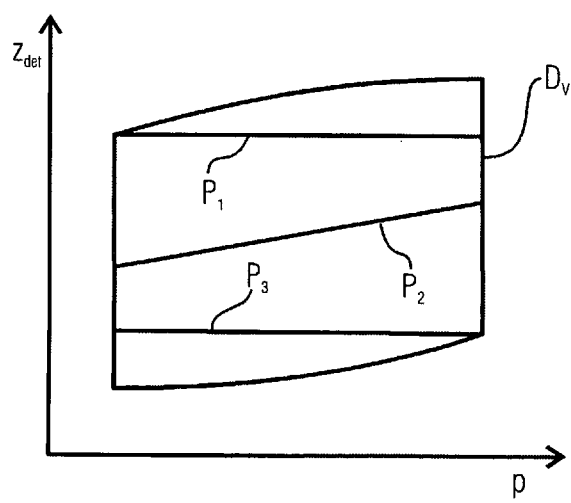
FIGS. 4a–4d show a representation of the projection of the segment planes on virtual detectors with a different projection angle.
Figure 4B:
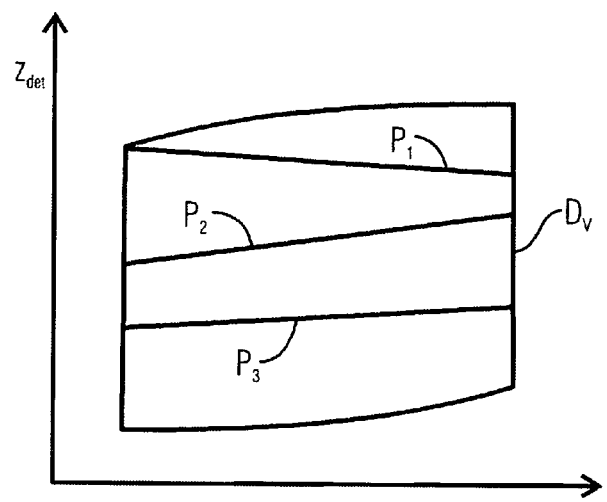
Figure 4C:
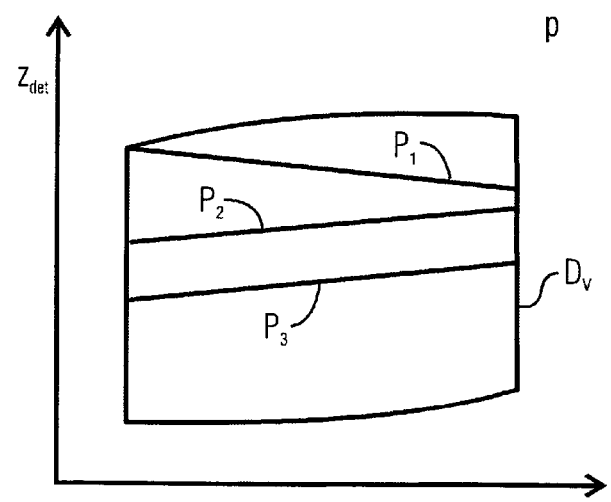
Figure 4D:
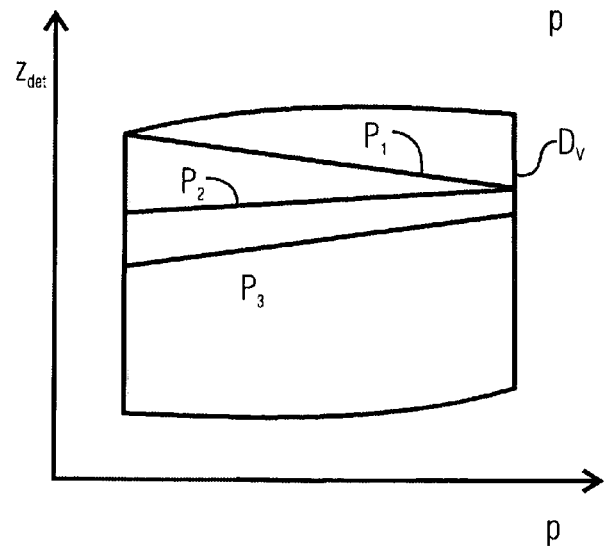

FIG. 3 shows the spiral track S of the measuring arrangement of the spiral CT, on which the focus F moves with the physical detector Dp situated opposite, conversion having already been carried out using parallel beam geometry in this representation. This may also be seen by virtue of the fact that in this image the focus F is shown in five juxtaposed positions with three parallel rays in each case. In the background, these parallel rays strike the physical detector Dp which, however, is already displaying one image of many detector positions of revolving detector elements. The detector image of the physical detector Dp is projected, furthermore, onto the virtual detector Dv, which adjoins the system axis. FIG. 3 also shows three exemplary planes of section E1 to E3, which are imaged on the detector Dv.

Considering the virtual detector Dv in the coordinated system solely with the representation of the projections P1 to P3 that correspond to the planes E1 to E3 from FIG. 3, the result is a representation of the virtual detector Dv such as is shown in FIGS. 4a to 4d. The successive displacement of projections in the FIGS. 4a to 4d is produced in this case by considering the planes E1 to E3 and their projections P1 to P3 for progressive rotation about the z-axis.

The idea of an embodiment of the invention resides also in also carrying out in the 3D reconstruction filtering which proceeds in the respective direction of projection of the plane considered. As may be seen from FIGS. 4a to 4d, the alignment of the projections changes from bottom to top continuously, and the filtering direction therefore does so likewise.

Figure 5:
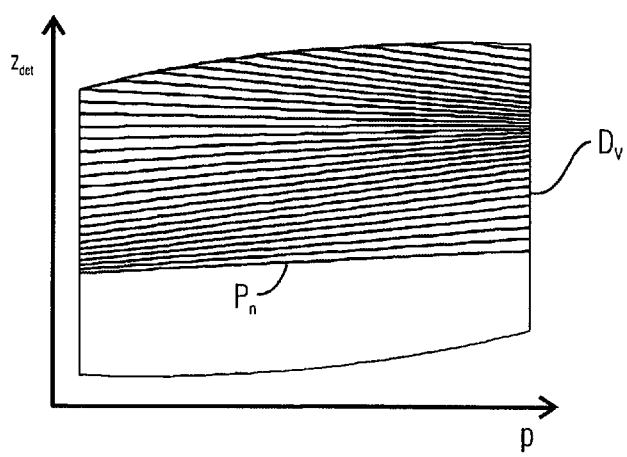
FIG. 5 shows a representation of the profile of projection planes with the aid of 16-row detector and a change in the filtering direction.

Consideration of the corresponding representation with a higher number of planes and projections results in a representation of the virtual detector as is shown in FIG. 5. The projections P in this case change their direction from bottom to top in a typical continuous way. According to the invention, two-dimensional filtering is carried out correspondingly for each detector image thus obtained in a fashion from left to right, the direction of filtering also being over the height of the detector in accordance with the direction in which the projections run.

Figure 6:
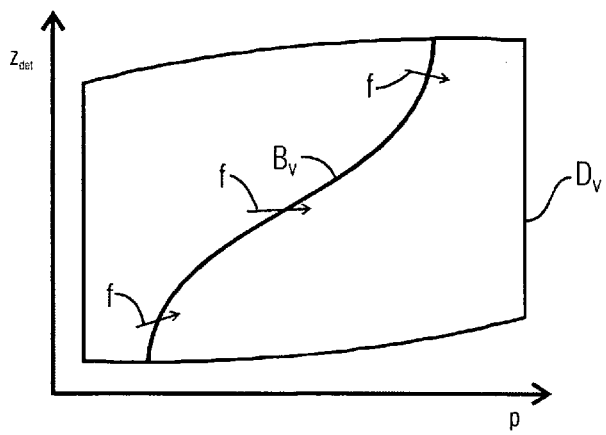
FIG. 6 shows an illustration of the migration of the projection of a voxel over the detector in the case of a progressive projection angle.

For the purpose of the 3D back projection, which relates to the voxel $V_{(x,y,z)}$, the rays that penetrate a voxel in this volume to be examined are considered so as to determine the absorptivity of a voxel. In the case of continuous revolution above the z-axis and projections of this one voxel $V_{(x,y,z)}$ onto the virtual detector Dv, the track of the projection of this voxel runs over the multiplicity of the detector images considered, as illustrated in FIG. 6 by the track Bv. Here, the line of section of a segment plane in the respective virtual detector is plotted for different directions of protection. 32 different directions of projection are considered in this case. The inventive method in this case filters the individual detector points in different directions f that respectively correspond to the direction of the projections of the segment plane which runs through this voxel. It may be pointed out in order to avoid misunderstandings that this number is not to be equated with the row number of the detector.

Figure 7:
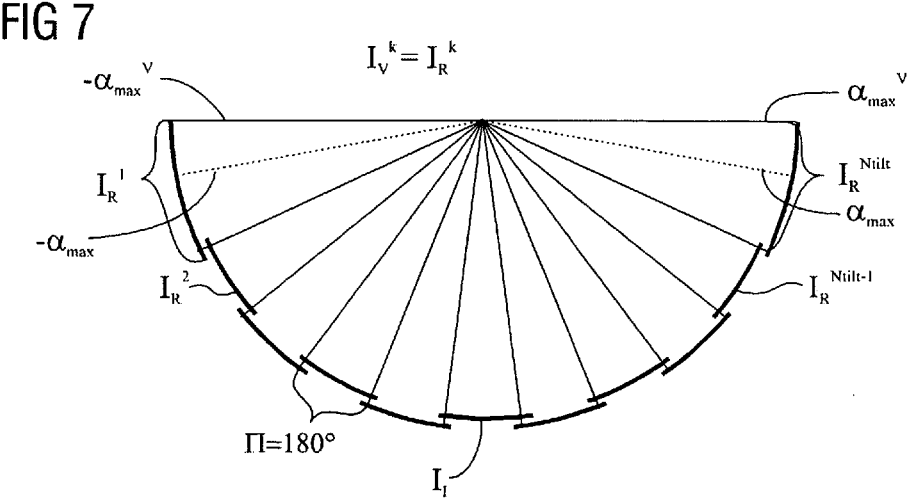
FIG. 7 shows a pictorial representation of the juxtaposed reconstruction segments of the reprojection of a voxel.

The voxel track Bv can be illustrated corresponds to a revolution of the measuring arrangement between $-\alpha_{max}^v$ and $+\alpha_{max}^v$. If this track is subdivided in the inventive way into reconstruction subsegments $I_R^1$ to $I_R^{Ntilt}$, these can thus be represented as shown in FIG. 7. It is to be pointed out in this case that the illustrated total angle from $-\alpha_{max}^v$ and $+\alpha^{maxv}$ is much larger than the 180° shown and corresponds to a plurality of revolutions of the measuring arrangement. With the exception of the segments positioned at the edge—segments are arranged equidistantly with reference to their centers and centroids, and in a slightly overlapping fashion.

The back projection of these reconstruction segments onto the voxel $V_{(x,y,z)}$ considered then gives the absorption value, assigned to this voxel, inside the object to be examined. If this mode of procedure is carried out to all the voxels in the entire considered volume to be examined, the result is a volumetric representation of the absorption values of the object to be examined.

Because if image voxel is imaged in each subsegment of the reconstruction region in the detector, each image voxel makes a contribution of the same weight to the reconstructured image volume. Consequently, there is no need for the measured data to be weighted by voxel.

Thus, in sum, an embodiment of the invention uses an imaging method for a multi-slice spiral CT with 3D back projection, and a spiral CT in which in order to reconstruct the absorption value from at least one voxel, use is made of the measured and filtered data that are produced by rays which penetrate this at least one voxel, the filtering of the data, used for the reconstruction, in the image of the virtual detector being performed in the direction of the projection of spiral segments that are imaged thereon and which are produced by spiral scanning over a prescribed angular range.

It may be pointed out in addition that the previously described method and CT can also be used to represent periodically moving objects, in particular for cardiological spiral CT, in which case it is necessary for relevant data to be weighted or selected in a way known per se and correlated with the situation of movement on the object to be examined.

Exemplary embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. An imaging method for a multi-slice spiral CT scan, comprising:
    spirally scanning an object to be examined, with reference to its absorption behavior;
    collecting measured absorption data using a detector;
    projecting the measured absorption data onto a virtual detector and filtering the data; and
    using measured and filtered data produced by rays that penetrate at least one voxel to reconstruct an absorption value of the at least one voxel, wherein
        the filtering of the data used for the reconstruction is performed in the direction of a projection of spiral segments that are imaged thereon, produced by the spiral scanning over a prescribed angular range, and wherein
        the filtering takes place along the intersection line of doubly inclined planes in the virtual detector.

2. The method as claimed in claim 1, wherein the segment planes formed at least approximately by the spiral segments have a maximum inclination such that rays for the segment plane in the detector are present inside the measuring field at the ends of the spiral segment considered.

3. The method as claimed in claim 1, wherein, for the purpose of 3D back projection a spiral segment $I_I$ of length $L_I=[-\alpha_{max}, +\alpha_{max}]$ with $\alpha_{max}=M \cdot \pi/p$ is subdivided equidistantly into $N_{tilt}$ overlapping partial segments $I_I^k$ ($1 \leq k \leq N_{tilt}$) of length $L_S$, whose centroids differ from one another by at most $L_S$, p corresponding to the set pitch, such that the following holds for the subsegments $I_R^k$ ($1 \leq k \leq N_{tilt}$) produced:

$$I_R^k = I_I^k; 1 < k < N_{tilt}$$

$$I_R^1 = I_I^1 \cup \{-\alpha^v \max, -\alpha \max\}$$

$$I_R^{Ntilt} = I_I^{Ntilt} \cup \{\alpha \max, \alpha^v \max\}$$

and the projection datum, belonging to an image voxel, in the detector image $D_k$ is determined by projection in the reconstruction segment $I_R^k$ ($1 \leq k \leq N_{tilt}$), $\alpha^V_{max}$ representing the maximum angle reached by the ray through the voxel V.

4. The method as claimed in claim 1, wherein the measured absorption data is weighted as a function of the cosine angle of the ray produced in the direction of the axis of rotation of the detector and radiation source.

5. The method as claimed in claim 1, wherein the detector is of planar design and includes a multiplicity of detector elements arranged matricially in rows and columns for detecting the spiral scanning.

6. The method as claimed in claim 1, wherein the scanning of the object is done by rotating ray bundle moving in the direction of the axis of rotation.

7. The method as claimed in claim 6, wherein the projecting of the measured absorption data onto a virtual detector is done at a fulcrum of the rotation.

8. The method as claimed in claim 7, wherein the collecting of the measured data is done by a detector of a planar design.

9. The method as claimed in claim 7, wherein the prescribed angular range for a spiral segment of length $L_s$ is $\leq \Pi + 2*\beta_{max}$.

10. The method as claimed in claim 7, wherein parallel sorting of the rays for the purpose for forming the virtual detector takes place before the filtering.

11. The method as claimed in claim 10, wherein the prescribed angular range for a spiral segment of length $L_s$ is $\leq 180°$.

12. The method as claimed in claim 7, wherein the segment planes formed at least approximately by the spiral segments have a maximum inclination such that rays for the segment plane in the detector are present inside the measuring field at the ends of the spiral segment considered.

13. The method as claimed in claim 7, wherein, for the purpose of 3D back projection a spiral segment $I_I$ of length $L_I=[-\alpha_{max}, +\alpha_{max}]$ with $\alpha_{max}=M \cdot \pi/p$ is subdivided equidistantly into $N_{tilt}$ overlapping partial segments $I_I^k$ ($1 \leq k \leq N_{tilt}$) of length $L_S$, whose centroids differ from one another by at most $L_S$, p corresponding to the set pitch, such that the following holds for the subsegments $I_R^k$ ($1 \leq k \leq N_{tilt}$) produced:

$$I_R^k = I_I^k; 1 < k < N_{tilt}$$

$$I_R^1 = I_I^1 \cup \{-\alpha^v \max, -\alpha \max\}$$

$$I_R^{Ntilt} = I_I^{Ntilt} \cup \{\alpha \max, \alpha^v \max\}$$

and the projection datum, belonging to an image voxel, in the detector image $D_k$ is determined by projection in the reconstruction segment $I_R^k$ ($1 \leq k \leq N_{tilt}$), $\alpha^V_{max}$ representing the maximum angle reached by the ray through the voxel V.

14. The method as claimed in claim 7, wherein the measured absorption data is weighted as a function of the cosine angle of the ray produced in the direction of the axis of rotation of the detector and radiation source.

15. The method as claimed in claim 7, wherein the measured absorption data is weighted as a function of the cosine angle of the ray produced in the direction of the axis of rotation of the detector and radiation source, the cosine angle being a cosine of its cone angle.

16. The method as claimed in claim 7, wherein the detector is of planar design and includes a multiplicity of detector elements arranged matricially in rows and columns for detecting the spiral scanning.

17. The method as claimed in claim 1, wherein the collecting of the measured data is done by a detector of a planar design.

18. The method as claimed in claim 1, wherein the prescribed angular range for a spiral segment of length $L_s$ is $\leq \Pi + 2*\beta_{max}$.

19. The method as claimed in claim 1, wherein parallel sorting of the rays for the purpose for forming the virtual detector takes place before the filtering.

20. The method as claimed in claim 19, wherein the prescribed angular range for a spiral segment of length $L_s$ is $\leq 180°$.

21. The method as claimed in claim 1, wherein the measured absorption data is weighted as a function of the cosine angle of the ray produced in the direction of the axis of rotation of the detector and radiation source, the cosine angle being a cosine of its cone angle.

22. The method as claimed in claim 1, wherein the prescribed angular range for a spiral segment of length $L_s$ is $\leq \Pi + 2*\beta_{max}$.

23. An imaging method for a multi-slice spiral CT scan, comprising:
   spirally scanning an object to be examined, with reference to its absorption behavior;
   collecting measured absorption data using a detector;
   projecting the measured absorption data onto a virtual detector and filtering the data; and
   using measured and filtered data produced by rays that penetrate at least one voxel to reconstruct an absorption value of the at least one voxel, wherein
      the filtering of the data used for the reconstruction is performed in the direction of a projection of spiral segments that are imaged thereon, produced by the spiral scanning over a prescribed angular range, and wherein
      the prescribed angular range for a spiral segment of length $L_s$ is $\leq \Pi + 2*\beta_{max}$.

24. The method as claimed in claim 23, wherein the segment planes formed at least approximately by the spiral segments have a maximum inclination such that rays for the segment plane in the detector are present inside the measuring field at the ends of the spiral segment considered.

25. The method as claimed in claim 23, wherein, for the purpose of 3D back projection a spiral segment $I_I$ of length $L_I = [-\alpha_{max}, +\alpha_{max}]$ with $\alpha_{max} = M \cdot \pi/p$, is subdivided equidistantly into $N_{tilt}$ overlapping partial segments $I_I^k$ ($1 \leq k \leq N_{tilt}$) of length $L_S$, whose centroids differ from one another by at most $L_S$, p corresponding to the set pitch, such that the following holds for the subsegments $I_R^k$ ($1 \leq k \leq N_{tilt}$) produced:

$$I_R^k = I_I^k; 1 < k < N_{tilt}$$

$$I_R^1 = I_I^1 \cup \{-\alpha^v \max, -\alpha \max\}$$

$$I_R^{Ntilt} = I_I^{Ntilt} \cup \{\alpha \max, \alpha^v \max\}$$

and the projection datum, belonging to an image voxel, in the detector image $D_k$ is determined by projection in the reconstruction segment $I_R^k$ ($1 \leq k \leq N_{tilt}$), $\alpha^V_{max}$ representing the maximum angle reached by the ray through the voxel V.

26. The method as claimed in claim 23, wherein the measured absorption data is weighted as a function of the cosine angle of the ray produced in the direction of the axis of rotation of the detector and radiation source.

27. The method as claimed in claim 23, wherein the detector is of planar design and includes a multiplicity of detector elements arranged matricially in rows and columns for detecting the spiral scanning.

28. The method as claimed in claim 23, wherein the scanning of the object is done by rotating ray bundle moving in the direction of the axis of rotation.

29. The method as claimed in claim 23, wherein the projecting of the measured absorption data onto a virtual detector is done at a fulcrum of the rotation.

30. The method as claimed in claim 23, wherein the filtering takes place along the intersection line of doubly inclined planes in the virtual detector.

31. A CT unit for scanning an object to be examined, comprising:
   at least one program or program module, which when carried out in the CT unit implements the method of claim 23.

32. An imaging method for a multi-slice spiral CT scan, comprising:
   spirally scanning an object to be examined, with reference to its absorption behavior;
   collecting measured absorption data using a detector;
   projecting the measured absorption data onto a virtual detector and filtering the data; and
   using measured and filtered data produced by rays that penetrate at least one voxel to reconstruct an absorption value of the at least one voxel, wherein
      the filtering of the data used for the reconstruction is performed in the direction of a projection of spiral segments that are imaged thereon, produced by the spiral scanning over a prescribed angular range,
      parallel sorting of the rays for the purpose for forming the virtual detector takes place before the filtering, and
      the prescribed angular range for a spiral segment of length $L_s$ is $\leq 180°$.

33. The method as claimed in claim 32, wherein the segment planes formed at least approximately by the spiral segments have a maximum inclination such that rays for the segment plane in the detector are present inside the measuring field at the ends of the spiral segment considered.

34. The method as claimed in claim 32, wherein, for the purpose of 3D back projection a spiral segment $I_I$ of length $L_I = [-\alpha_{max}, +\alpha_{max}]$ with $\alpha_{max} = M \cdot \pi/p$ is subdivided equidistantly into $N_{tilt}$ overlapping partial segments $I_I^k$ ($1 \leq k \leq N_{tilt}$) of length $L_S$, whose centroids differ from one another by at most $L_S$, p corresponding to the set pitch, such that the following holds for the subsegments $I_R^k$ ($1 \leq k \leq N_{tilt}$) produced:

$$I_R^k = I_I^k; 1 < k < N_{tilt}$$

$$I_R^1 = I_I^1 \cup \{-\alpha^v \max, -\alpha \max\}$$

$$I_R^{Ntilt} = I_I^{Ntilt} \cup \{\alpha \max, \alpha^v \max\}$$

and the projection datum, belonging to an image voxel, in the detector image $D_k$ is determined by projection in the reconstruction segment $I_R^k$ ($1 \leq k \leq N_{tilt}$), $\alpha^V_{max}$ representing the maximum angle reached by the ray through the voxel V.

35. The method as claimed in claim 32, wherein the measured absorption data is weighted as a function of the cosine angle of the ray produced in the direction of the axis of rotation of the detector and radiation source.

36. The method as claimed in claim 32, wherein the detector is of planar design and includes a multiplicity of detector elements arranged matricially in rows and columns for detecting the spiral scanning.

37. The method as claimed in claim 32, wherein the scanning of the object is done by rotating ray bundle moving in the direction of the axis of rotation.

38. The method as claimed in claim 32, wherein the projecting of the measured absorption data onto a virtual detector is done at a fulcrum of the rotation.

39. The method as claimed in claim 32, wherein the filtering takes place along the intersection line of doubly inclined planes in the virtual detector.

40. A CT unit for scanning an object to be examined, comprising:
  at least one program or program module, which when carried out in the CT unit implements the method of claim 32.

41. A CT unit for scanning an object to be examined, comprising:
  a ray bundle emanating from at least one focus;
  a detector array of planar design, including a multiplicity of distributed detector elements for detecting the rays of the ray bundle, the at least one focus being adapted to move relative to the object on at least one focal track running around the object, wherein the detector array is situated opposite thereto; and
  means for collecting the detector data, filtering and back-projecting the data, wherein
    the measured and filtered data produced by rays that penetrate at least one voxel are used to reconstruct an absorption value of the at least one voxel, the filtering of the data being performed in the direction of a projection of spiral segments that are imaged thereon, produced by the spiral scanning over a prescribed angular range,
    the means for filtering is implemented at least partially by at least one program or program module, and
    the filtering takes place along the intersection line of doubly inclined planes in the virtual detector.

42. An imaging method for a multi-slice spiral CT scan, comprising:
  spirally scanning an object to be examined, with reference to its absorption behavior;
  collecting measured absorption data using a detector;
  projecting the measured absorption data onto a virtual detector and filtering the data; and
  using measured and filtered data produced by rays that penetrate at least one voxel to reconstruct an absorption value of the at least one voxel, wherein
    the filtering of the data used for the reconstruction is performed in the direction of a projection of spiral segments that are imaged thereon, produced by the spiral scanning over a prescribed angular range, and
    for the purpose of 3D back projection a spiral segment $I_I$ of length $L_I=[-\alpha_{max}, +\alpha_{max}]$ with $\alpha_{max}=M\cdot\pi/p$, is subdivided equidistantly into $N_{tilt}$ overlapping partial segments $I_I^k$ ($1 \leq k \leq N_{tilt}$) of length $L_S$, whose centroids differ from one another by at most $L_S$, p corresponding to the set pitch, such that the following holds for the subsegments $I_R^k$ ($1 \leq k \leq N_{tilt}$) produced:

$I_R^k = I_I^k; 1 < k < N_{tilt}$ $I_R^1 = I_I^1 \cup \{-\alpha^v \max, -\alpha \max\}$ $I_R^{Ntilt} = I_I^{Ntilt} \cup \{\alpha \max, \alpha^v \max\}$ and the projection datum, belonging to an image voxel, in the detector image $D_k$ is determined by projection in the reconstruction segment $I_R^k$ ($1 \leq k \leq N_{tilt}$), $\alpha^V_{max}$ representing the maximum angle reached by the ray through the voxel V.

43. The method as claimed in claim 42, wherein the measured absorption data is weighted as a function of the cosine angle of the ray produced in the direction of the axis of rotation of the detector and radiation source.

44. The method as claimed in claim 42, wherein the detector is of planar design and includes a multiplicity of detector elements arranged matricially in rows and columns for detecting the spiral scanning.

45. The method as claimed in claim 42, wherein the scanning of the object is done by rotating ray bundle moving in the direction of the axis of rotation.

46. The method as claimed in claim 42, wherein the projecting of the measured absorption data onto a virtual detector is done at a fulcrum of the rotation.

47. The method as claimed in claim 42, wherein the collecting of the measured data is done by a detector of a planar design.

48. The method as claimed in claim 42, wherein the filtering takes place along the intersection line of doubly inclined planes in the virtual detector.

49. A CT unit for scanning an object to be examined, comprising:
  at least one program or program module, which when carried out in the CT unit implements the method of claim 42.

* * * * *